(12) United States Patent
Doubler et al.

(10) Patent No.: US 8,157,801 B2
(45) Date of Patent: Apr. 17, 2012

(54) INTRAMEDULLARY SCREW AND TANG FOR ORTHOPEDIC SURGERY

(76) Inventors: Robert L. Doubler, Ida, MI (US); John E. Hammill, Rossford, OH (US)

( * ) Notice: Subject to any disclaimer, the term of this patent is extended or adjusted under 35 U.S.C. 154(b) by 1103 days.

(21) Appl. No.: 10/776,008

(22) Filed: Feb. 9, 2004

(65) Prior Publication Data

US 2005/0177158 A1 Aug. 11, 2005

(51) Int. Cl.
*A61B 17/56* (2006.01)
(52) U.S. Cl. .......................................................... 606/64
(58) Field of Classification Search .............. 606/62–68, 606/72, 73
See application file for complete search history.

(56) References Cited

U.S. PATENT DOCUMENTS

| | | | | |
|---|---|---|---|---|
| 3,791,380 A | * | 2/1974 | Dawidowski | 606/68 |
| 4,236,512 A | | 12/1980 | Aginsky | |
| 4,275,717 A | * | 6/1981 | Bolesky | 606/63 |
| 4,453,539 A | | 6/1984 | Raftopoulos et al. | |
| 4,590,930 A | | 5/1986 | Kurth et al. | |
| 5,534,004 A | * | 7/1996 | Santangelo | 606/68 |
| 5,810,820 A | * | 9/1998 | Santori et al. | 606/63 |
| 6,183,474 B1 | * | 2/2001 | Bramlet et al. | 606/66 |
| 6,443,954 B1 | | 9/2002 | Bramlet et al. | |
| 6,447,546 B1 | * | 9/2002 | Bramlet et al. | 623/17.16 |
| 6,488,684 B2 | | 12/2002 | Bramlet et al. | |
| 6,558,388 B1 | * | 5/2003 | Bartsch et al. | 606/62 |
| 7,118,572 B2 | * | 10/2006 | Bramlet et al. | 606/66 |

* cited by examiner

*Primary Examiner* — Nicholas Woodall
(74) *Attorney, Agent, or Firm* — McHale & Slavin, P.A.

(57) ABSTRACT

One method of reducing fractures in long bones is to insert an intramedullary screw through the bone canal across the fracture and deploy tangs to increase the purchase of the screw. Compression is then applied along the screw to bring the broken bone together. An improved low cost lag screw has a cannulated shaft with a shaped bore in the leading end. A similarly shaped tang body is movably disposed in the leading end bore. The tang body has several tangs laser welded about the periphery and extending from the tang body. The shaped surfaces of the bore have exit holes and the ends of the tangs are adjacent the holes. An end cap is laser welded to the leading end of the shaft.

17 Claims, 3 Drawing Sheets

INTRAMEDULLARY SCREW AND TANG FOR ORTHOPEDIC SURGERY

FIELD OF THE INVENTION

The present invention generally relates to an intramedullary system for coupling first and second bone portions across a fracture therebetween.

BACKGROUND OF THE INVENTION

In the 1960s, the compression hip screw was introduced, resulting in improved fixation of the proximal femur. A lag screw assembly was inserted into the femoral head, a plate was attached to the lateral femur, and a compression screw joined the two. These implants provided a more rigid structure for the patient and allowed the surgeon to compress the fractured fragments against each other thereby decreasing the time to mobility. A number of compression hip screws have been introduced for fracture fixation about the proximal femur.

Newer devices and inventions explored additions to the nail and lag screw assembly to improve the fixation and ease or eliminate the need to locate the distal screw holes. These newer devices are commonly classified as "expanding devices" and expand in size, after placement, to fill the intramedullary cavity. In these patents a mechanism is actuated deploying arms or anchor blades through the cancellous bone to contact the inner cortical wall.

Other expanding devices provide surface contact with the internal cortical wall resulting in a wedge effect. Kurth, U.S. Pat. No. 4,590,930, Raftopoulos, U.S. Pat. No. 4,453,539 and Aginski, U.S. Pat. No. 4,236,512 among others have described mechanisms which deploy or expand with a molly bolt concept. These methods are complex and difficult to retract should the nail or lag screw assembly require extraction and do not deploy through the cortical bone.

In U.S. Pat. Nos. 6,443,954 and 6,488,684, both incorporated herein by reference and shown in FIG. 1 as prior art, Bramlet describes a surgical anchor which has deployable tangs. These tangs are simple in design, internally positioned, yet easily deployed into, and if desired through, the cortical bone providing improved purchase for compression of a fracture; especially in osteogenic bone. These tangs are just as easily retracted.

The tang body and the tangs of these devices are made of one piece. The tang body, in each of these devices, is round with a leading protrusion rectangularly shaped for registering the tangs with the tang exit holes. The tangs are also triangular and the tang exit holes are circular. In production, these devices require very precise tolerances, machining and assembly which results in high costs.

What is needed in the art is a low cost surgical screw that can be made of non-complex components made from different materials or combinations of materials and using easily controlled manufacturing steps.

SUMMARY OF THE PRESENT INVENTION

An improved surgical intramedullary system for compressing fractures having an elongated cannulated shaft with tang exit holes and at least one deployable tang, the improvement comprising an end cap bonded to one end of the cannulated shaft by a first bond, a tang body slidably disposed in one end of the cannulated shaft, the internal wall of the cannulated shaft and the external surface of the tang body congruently shaped to restrict movement of the tang body to the longitudinal axis of the cannulated shaft. The tang having a first end and a second end, the first end bonded to the tang body by a second bond. The second end adapted to transit one tang exit hole in the cannulated shaft upon longitudinal movement of the tang body, the tang body including a link adapted to cooperate with a tool to generate longitudinal movement.

Therefore, it is an objective of this invention to teach a surgical intramedullary screw having simple components which can be quickly assembled to produce the finished product.

It is another objective of this invention to teach forming each of the components by easily controlled steps reducing production costs.

It is a further objective of this invention to teach a surgical screw structure and fabrication permitting combination of materials having different properties into one screw.

It is still another objective of this invention to teach permanently bonding components to prevent avoid disassembly.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

SHORT DESCRIPTION OF THE DRAWINGS

DETAILED DESCRIPTION OF THE INVENTION

Figure 1:
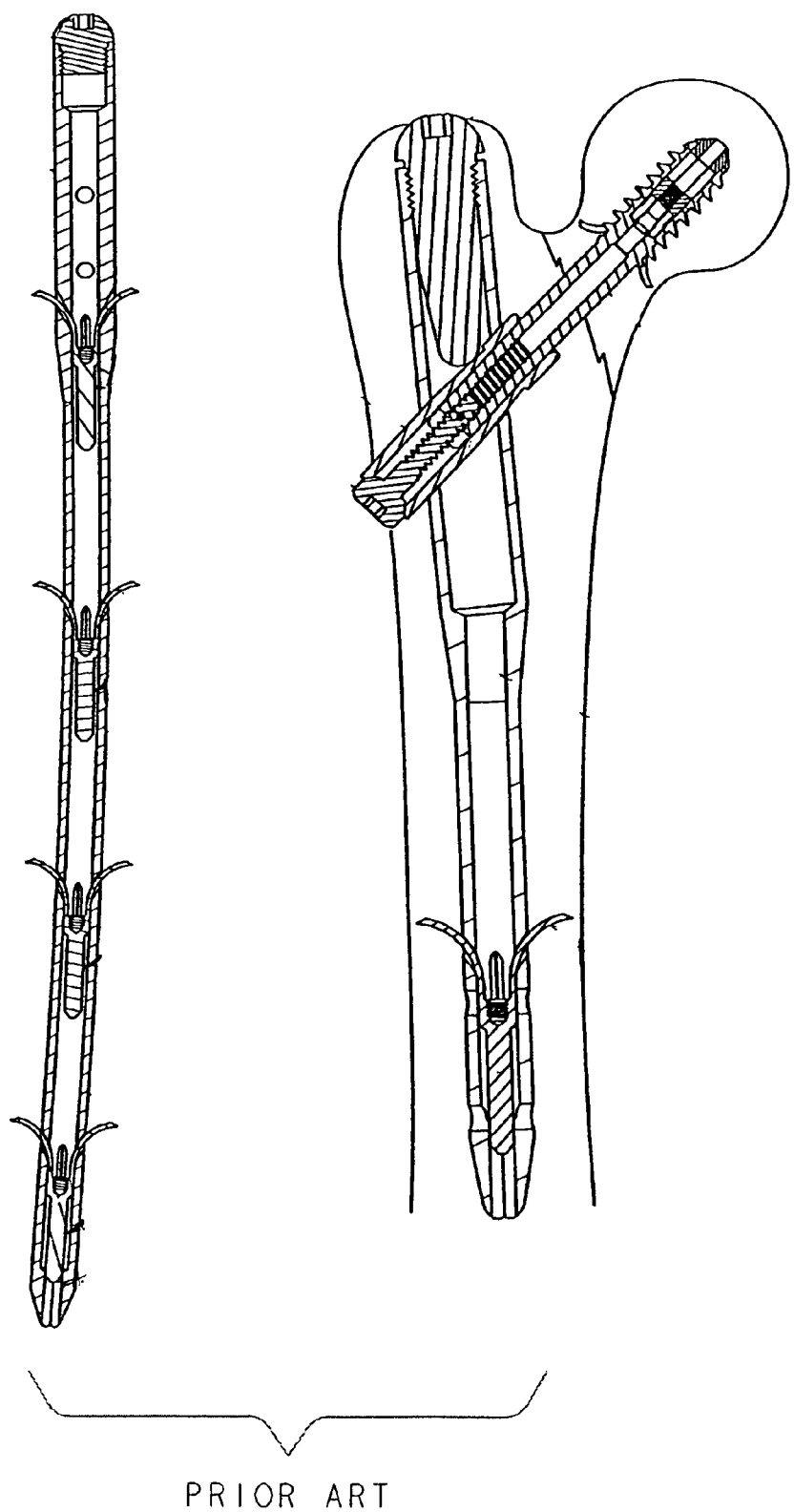
FIG. 1 is a cross section of intramedullary screws of the prior art.

In FIG. 1, prior art intramedullary screws used for applying compression across a fracture are illustrated. The tang body is formed as a complex one piece component with a tang body and tangs which generally requires a single choice of material. To change the dimensions or the materials for the tangs, relative to the tang body, requires the component to be changed, as a whole.

The tang body has a protrusion on the leading end which acts as a guide to register the tangs with the exit holes. The tang body has a threaded blind bore for engaging a tool for deploying the tangs. The tool is threaded into the bore and then a retrograde pulling force is exerted on the tool to displace the tangs through the exit holes. This results in a force acting to dislodge the screw.

The leading end of the intramedullary screws are formed of a one piece construction with the shaft of the screw. Therefore, the tang body must be inserted through the length of the screw which requires that the entire bore of the screw be machined to match the tang body. The shaped surfaces guiding the tang body through the aperture at the leading end must be precisely oriented with the exit holes though there is no structural guide to orient these two components. Further, the approach to these components is from the trailing end of the screw. During surgery, because the tang body blocks the leading aperture, the guide wire used to place the screw, across the fracture, must be removed before the tang body can be inserted. The pushing of the tang body through the bore may shift the axis of the screw without guidance.

The leading end of the lag screw shown in the prior art appears to have an end cap separate from the shaft of the lag screw however, there is no indication of the specific connection between the shaft and the end cap. The lag screws of the prior art include a compression screw threaded into the trailing end of the lag screw to provide compression across the fracture, as is also the case in the instant invention.

Figure 2:
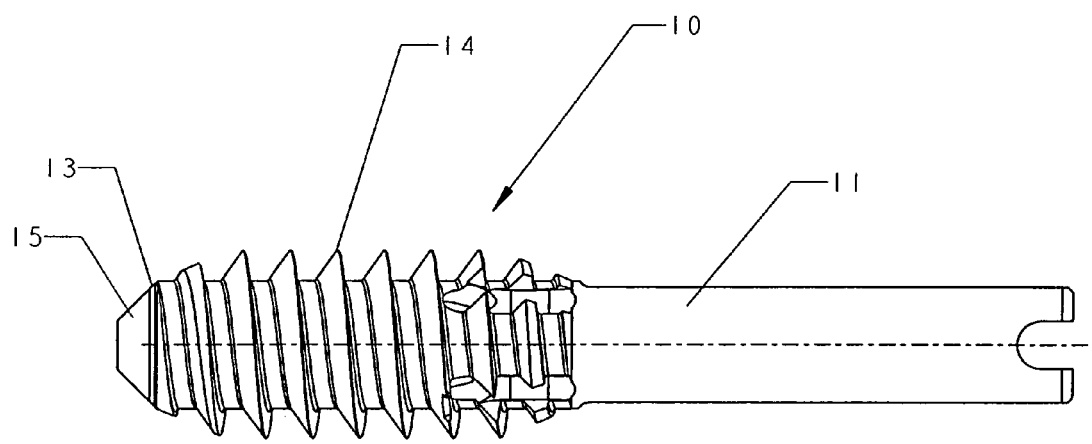
FIG. 2 is a perspective view of a surgical lag screw of this invention.
Figure 3:
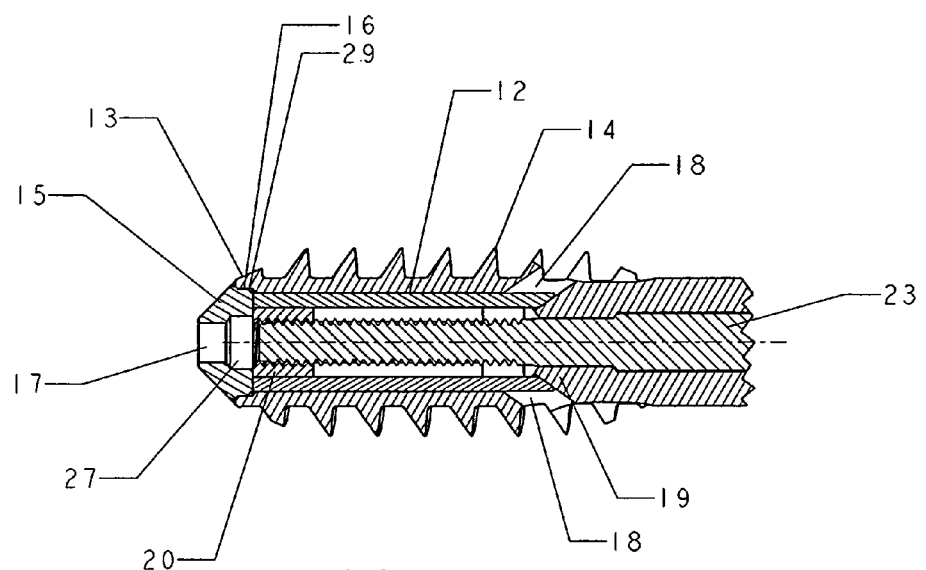
FIG. 3 is a longitudinal cross section of FIG. 2.

The cannulated lag screw 10, shown in FIG. 2, has a shaft 11, a bore 12 and a leading end 13. The shaft has external threads 14 near the leading end and the shaft is closed with an end cap 15. The leading end of the bore 12 has an enlarged counter bore 29. The end cap 15 has a skirt 16 in contact with the shaft 11 within the counter bore 29. The end cap has a central aperture 17 sized to telescope along a guide wire (not shown).

The bore 12 extends from the trailing end of the screw to the leading end and has a inner diameter to slide over a guide wire and through which a tool, similar to a draw bolt, may be telescoped.

Within the leading end of the screw 10, the inner diameter is greater than the bore in the trailing end. The internal walls of the leading end of the bore 12 are shaped by intersecting planar surfaces. These surfaces extend, within the bore, throughout the portion of the leading end carrying the external threads 14. As illustrated, the intersecting surfaces form an octagonal cross section in the bore. Of course, other geometric shapes may be used. The relatively short octagonal shaped surfaces are formed through the leading end by EDM (electrical discharge machining), broaching or extrusion.

The external threads 14 have tang exit holes 18 spaced about their circumference. The exit holes extend from the bore through the shaft. Their location is positively related to the position of the planar surfaces of the internal walls with each hole formed in a planar surface. The preferred orientation is at ninety degrees providing 4 tang exit holes around the screw. The holes 18 are shown as circular but other shapes may be employed.

The short octagonal shaped surfaces extend from the leading end to the tang exit holes 18. The remaining lesser diameter of the bore 12 forms a shoulder 19 about the tang exit holes 18.

Figure 4:
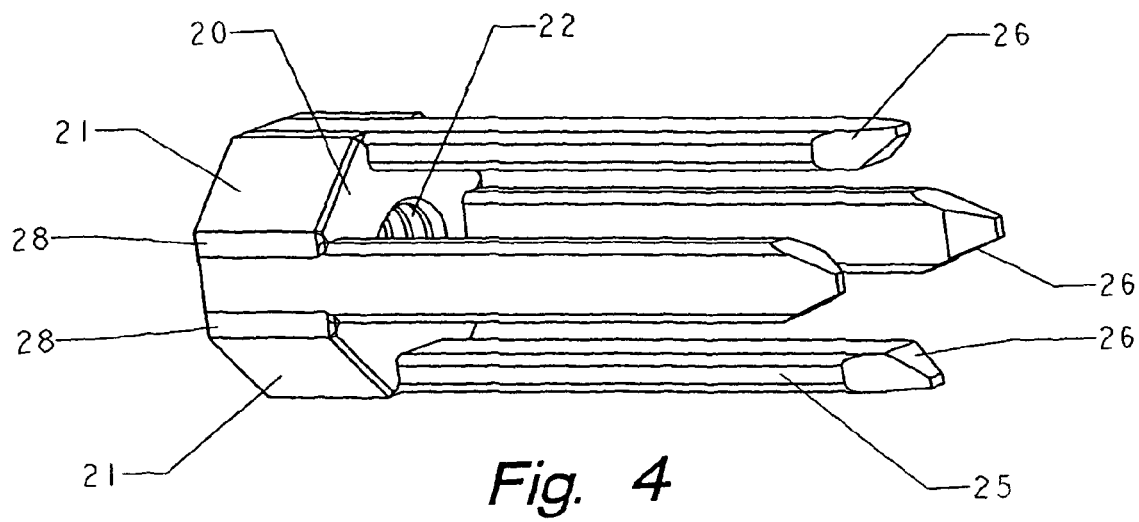
FIG. 4 is a perspective view of the tangs and tang body of this invention.
Figure 5:
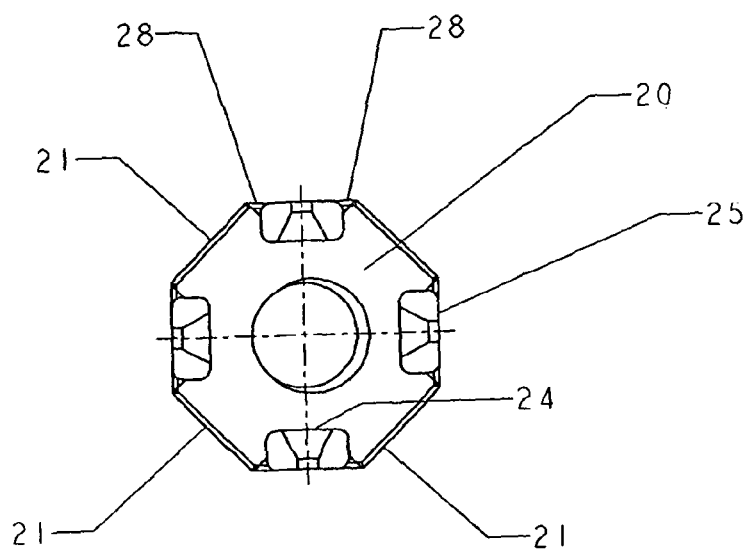
FIG. 5 is and end view of the tang body of this invention.

The tang body 20, shown in FIG. 4, is formed with a shape commensurate with the intersecting planar surfaces of the leading end bore 12. For example, the tang body 20 has an external octagonal shaped sides 21 to match the illustrated leading end bore. This shape prevents the tang body from rotating as the tangs are deployed and limits the translation of the tang body to the longitudinal axis of said bore. The tang body 20 includes an aperture with internal threads 22. The threads engage the tool 23 and act to translate the tang body upon turning the tool.

Grooves 24 may be cut, machined, extruded or otherwise formed in the planar surfaced sides 21 of the tang body. As shown, the grooves are rectilinear and of dimensions to accept a separate tang 25. Each planar surface may be grooved or the number of grooves may match the number of exit holes in the shaft. As shown, the tang body 20 has 4 grooves 24 spaced at 90 degrees about the circumference of the tang body.

Each groove 24 has a tang 25 laid in and bonded by a laser weld 28 to the tang body. The tangs are shown as rectangular in cross section but other shapes may be used. The ends 26 of the tangs are shown as chamfered to reduce the bending moment and guide the tangs 25 into the tang exit holes 18. The rectangular shape allows for easy control of the bending moment by changing the thickness, for example, without altering the surface area of the tang in contact with the bone.

This construction permits the use of different materials in the tang body and the tangs or the use of the same materials with differing characteristics. For example, the tang body may be of titanium of one degree of hardness and the tangs may be titanium of a lesser hardness. Further, all the components may be of the same material, such as titanium, or the components may be of different materials. The selection of materials is limited only by compatibility without reaction, ability to form a inter-bond by laser welding, strength, and being non-reactive biologically, to include surgical stainless steel and alloys, ceramics, and polymeric materials. While laser welding is the preferred bonding process, other welding processes may be used, as well as, heat and pressure to produce an autologous connection between the components.

The end cap 15 has a central aperture 17 for passage of a guide wire for placement of the intramedullary screw during surgery. The aperture 17 connects to the bore 12 through the threaded aperture in the tang body and provides a passage through the entire screw permitting the fully assembled intramedullary screw to be placed by the surgeon. The end cap has a smaller diameter skirt 16 fitting within the bore 12. The aperture 17 has a larger diameter countersunk cavity 27 within the skirt portion of the end cap. The clearance area 27 forms a bearing surface for the forward end of the tool 23. The end cap is laser welded to the leading end of the shaft.

A number of embodiments of the present invention have been described. Nevertheless, it will be understood that various modifications may be made without departing from the spirit and scope of the invention. Accordingly, it is to be understood that the invention is not to be limited by the specific illustrated embodiment but only by the scope of the appended claims.

What is claimed is:

1. In a surgical intramedullary system for compressing fractures having an elongated cannulated shaft with tang exit holes and at least one deployable tang, the improvement comprising a tang body slidably disposed in one end of said cannulated shaft, said at least one deployable tang formed separate from said tang body with a first end and a second end, said first end bonded to said tang body, said second end adapted to transit one tang exit hole in said cannulated shaft upon longitudinal movement of said tang body, said tang body including a link adapted to cooperate with a tool to generate longitudinal movement;

wherein said tang body is formed of a first material, and said at least one deployable tang is formed of a second material, said materials being compatible to produce a permanent bond.

2. The surgical intramedullary system of claim 1, wherein said bond is formed by laser welding.

3. The surgical intramedullary system of claim 1, wherein said tang body is formed of titanium having a first degree of hardness, and said at least one deployable tang is formed of titanium of a second lesser degree of hardness whereby said at least one deployable tang is adapted to deform during transit through said exit holes.

4. The surgical intramedullary system of claim 3, wherein said at least one deployable tang has a rectilinear shape defining planar sides having dimensions, said dimensions affecting said deforming of said at least one tang.

5. The surgical intramedullary system of claim 4, wherein an external surface of said tang body has planar sections, said first end of said at least one separate tang bonded to a planar section.

6. The surgical intramedullary system of claim 1, wherein said cannulated shaft and said end cap are formed of titanium.

7. The surgical intramedullary system of claim 6, wherein said first bond and said second bond are formed by laser welding.

8. The surgical intramedullary system of claim 1, wherein said link is composed of a central aperture through said tang body, said aperture having internal draw bolt threads.

9. The surgical intramedullary system for compressing fractures of claim 1, further including an end cap bonded to one end of said shaft.

10. The surgical intramedullary system for compressing fractures of claim 1, wherein an internal wall of said cannulated shaft and an external surface of said tang body are congruently shaped to restrict movement of said tang body to the longitudinal axis of said cannulated shaft.

11. In a surgical orthopedic system for repair of bones including an elongated cannulated shaft for placement in the intramedullary canal, said cannulated shaft having radial exit holes, a tang body movably disposed in said cannulated shaft, said tang body having attached elongated tangs adapted to transit said exit holes, and an end cap, the improvement comprising providing a plurality of separate deployable elongated tangs uniformly disposed about the surface of said tang body, each of said plurality of separate deployable elongated tangs permanently attached at one end to said tang body by laser welding, each of said plurality of deployable tangs having a rectilinear cross section for precise control of bending moment, said tang body having a central aperture with internal threads adapted to engage a draw bolt whereby said plurality of separate elongated tangs transit said exit holes as said tang body slides through said cannulated shaft;

wherein said tang body is formed of a first material, and said deployable tangs are formed of a second material, said materials being compatible to produce a permanent bond.

12. The surgical orthopedic system for repair of bones of claim 11, wherein said cannulated shaft, said end cap and said plurality of tangs are constructed from titanium, said tangs having a lesser degree of hardness than the degree of hardness of said tang body whereby the transit force is adjusted.

13. The surgical orthopedic system for repair of bones of claim 11, wherein said cannulated shaft has a plurality of intersecting planar internal walls, said tang body has a plurality of intersecting planar exterior surfaces said planar internal walls and said planar exterior surfaces combining to restrict sliding of said tang body to a longitudinal direction.

14. The surgical orthopedic system for repair of bones of claim 13, wherein each of said plurality of separate deployable elongated tangs are welded to a planar exterior surface of said tang body and said plurality of separate deployable elongated tangs numbers 4.

15. A surgical system comprising a intramedullary screw with an elongated cannulated shaft having a leading end and a trailing end, said cannulated shaft having shaped internal walls near said leading end and a plurality of tang exit holes in said shaft, a tang body slidably disposed near said leading end of said shaft, said tang body having an external shape congruent with said internal walls of said cannulated shaft, said tang body having a plurality of separate deployable tangs bonded to said tang body about said external shape, said external shape of said tang body and said shaped internal walls of said shaft registering said separate tangs and said tang exit holes, an end cap on said one end of said shaft having an aperture, said intramedullary screw made by the steps of:

(a) fabricating a tubular screw having an internal bore, said bore having a larger diameter near said leading end, forming intersecting planar surfaces on the sides of said larger diameter internal bore and radial exit holes therefrom;

(b) forming an end cap of a size to close said bore at said leading end;

(c) forming a tang body having an external surface with intersecting planar surfaces, said surfaces congruent with said planar surfaces on said internal sides of said bore, forming grooves in said intersecting planar surfaces and forming a central aperture internally screw threaded;

(d) forming a plurality of separate deployable elongated rectangular tangs having a length, width and height, chamfering one end of each of said plurality of tangs;

(e) placing one of said plurality of separate elongated rectangular tangs in each of said grooves in said tang body and laser welding said tang and said tang body together; and (f) assembling said tubular screw and said tang body by sliding said tang body in said leading end of said screw with said separate elongated rectangular tangs disposed adjacent said exit holes; and (g) bonding said end cap to said one end by laser welding;

wherein said tang body is formed of a first material, and said separate deployable tangs are formed of a second material, said materials being compatible to produce a permanent bond.

16. The surgical system of claim 15 including the steps of:
(a) forming a shoulder in said bore adjacent said exit holes; and
(b) sliding said tang body in said leading end to place said chamfered ends of said tangs adjacent said shoulder.

17. The surgical system of claim 15 including the steps of:
(a) inserting a tool through said bore from said trailing end to said leading end, said tool having draw threads on the forward end;
(b) turning said tool to engage said threads in said tang body and said draw threads on said tool; and
(c) said turning of said tool translating said tangs through said tang exit holes when said tool contacts said end cap.

* * * * *